United States Patent [19]

Lowell

[11] Patent Number: 5,726,292
[45] Date of Patent: Mar. 10, 1998

[54] IMMUNO-POTENTIATING SYSTEMS FOR PREPARATION OF IMMUNOGENIC MATERIALS

[76] Inventor: George H. Lowell, 6303 Westlin Run Dr., Baltimore, Md. 21215

[21] Appl. No.: 143,365

[22] Filed: Oct. 29, 1993

Related U.S. Application Data

[63] Continuation-in-part of Ser. No. 29,666, Mar. 11, 1993, abandoned, which is a continuation-in-part of Ser. No. 336,952, Apr. 12, 1989, abandoned, and a continuation-in-part of Ser. No. 642,093, Jan. 16, 1991, abandoned, which is a continuation of Ser. No. 65,440, Jun. 23, 1987, abandoned.

[51] Int. Cl.$^6$ .......................... C07K 1/107; C12P 21/02
[52] U.S. Cl. .................. 530/403; 424/185.1; 424/269.1; 435/69.3; 435/69.7; 435/172.3; 530/350; 530/395; 530/402; 530/404
[58] Field of Search ..................... 424/185.1, 186.1, 424/187.1, 188.2, 191.1, 268.1, 269.1; 435/69.3, 69.7, 172.3; 530/350, 395, 402, 403, 404

[56] References Cited

PUBLICATIONS

Lowell et al., "Proteosome–Lippeptide Vaccines: Enhancement of Immunogenicity for Malaria CS Peptides," *Science* 240:800–802, 6 May 1988.

Fahey et al., "Status of Immune–based Therapies in HIV Infection and AIDS," *Clin. Exp. Immunol.* 88:1–5, 1992.

Fox, J.L., "No Winners Against AIDS," *Biol Technology* 12:128, Feb. 1994.

Lowell et al. "Peptides to Proteosomes Via Hydrophobic Feet Become Highly Immunogenic Without Adjuvants," *J. Exp. Med.* 167:658–663, Feb. 1988.

Smith et al., "The Role of Lauroyl and Cys–Tyr–Gly–Gly In T Cell Activation by Synthetic Peptides From *Aasmdium falcipariana* Circumsporozoite Protein," *Technological Advances in Vaccine Development*, Alan R. Liss, Pub., pp. 651–659.1988.

W. Arraham et al., "Construction of a Synthetic Anti–HIV Vaccine: Role of the Nature of Carrier and Peptide Presentation," *VII Int'l Conf on AIDS*, Florence, Italy, Abstract No TH.A.67, Jun. 1991.

Yang et al; "Identification and Characterization of Host–Protective T Cell Epitopes of a Major Surface Exoprotein(gpb3) from *Leishmanin major*," *Immunology* 72:3–9, 1991.

Primary Examiner—Robert D. Budens
Attorney, Agent, or Firm—Cushman Darby & Cushman IP Group of Pillsbury Madison & Sutro LLP

[57] ABSTRACT

The invention is directed to improved immunopotentiating systems for preparation of immunogenic materials. More particularly, the invention is directed to immunogenic compositions containing a protein, polypeptide, or peptide, a hydrophobic anchor, and a proteosome. The immunogenic compositions are suitable for use as therapeutic agents and vaccines.

15 Claims, No Drawings

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

Phe  Leu  Leu  Ala  Val
    1                      5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

Phe  Leu  Leu  Ala  Val
    1                      5

( 2 ) INFORMATION FOR SEQ ID NO:3:

( i ) SEQUENCE CHARACTERISTICS:

(A) LENGTH: 14 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

Tyr Gly Gly Gly Cys Thr Gln Ile Thr Glu Pro Thr Cys Asn
1               5                   10

(2) INFORMATION FOR SEQ ID NO:4:

(i) SEQUENCE CHARACTERISTICS:
(A) LENGTH: 11 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

Tyr Gly Val Pro Val Ala Gln Thr Gln Thr Gly
1               5                   10

(2) INFORMATION FOR SEQ ID NO:5:

(i) SEQUENCE CHARACTERISTICS:
(A) LENGTH: 12 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:5:

Cys Tyr Gly Val Pro Val Ala Gln Thr Gln Thr Gly
1               5                   10

(2) INFORMATION FOR SEQ ID NO:6:

(i) SEQUENCE CHARACTERISTICS:
(A) LENGTH: 30 amino acids
(B) TYPE: amino acid
(C) STRANDEDNESS: single
(D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:6:

```
Cys Tyr Gly Val Pro Val Ala Gln Thr Gln Thr Gly Val Pro Val Ala
1                5                   10                  15

Gln Thr Gln Thr Gly Val Pro Val Ala Gln Thr Gln Thr Gly
            20                  25                  30
```

( 2 ) INFORMATION FOR SEQ ID NO:7:

( i ) SEQUENCE CHARACTERISTICS:
        ( A ) LENGTH: 47 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
Tyr Gly Val Pro Val Ala Gln Thr Gln Thr Gly Val Pro Val Ala Gln
1                5                   10                  15

Thr Gln Thr Gly Val Pro Val Ala Gln Thr Gln Thr Gly Val Pro Val
            20                  25                  30

Ala Gln Thr Gln Thr Gly Val Pro Val Ala Gln Thr Gln Thr Gly
            35                  40                  45
```

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

```
Lys Tyr Asn Ala Thr Lys Ala
1                5
```

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

```
Cys Lys Tyr Asn Ala Thr Lys Ala
1                5
```

( 2 ) INFORMATION FOR SEQ ID NO:10:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

```
Phe Leu Leu Ala Val Tyr Gly Gly Gly Cys Thr Gln Ile Thr Glu Pro
1               5                   10                  15

Thr Cys Asn
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:11:

```
Gly Gly Tyr Cys Phe Val Ala Leu Leu Phe
1               5                   10
```

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: unknown ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

```
GGTGGTTACT GCTTCGTTGC TCTGCTGTTC TGAG                               34
```

( 2 ) INFORMATION FOR SEQ ID NO:13:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: unknown ( i i ) MOLECULE TYPE: peptide ( i i i ) HYPOTHETICAL: NO ( i v ) ANTI-SENSE: NO ( v ) FRAGMENT TYPE: internal (x i) SEQUENCE DESCRIPTION: SEQ ID NO:13:

```
Asn Ala Asn Pro Asn Ala Asn Pro Asn Ala Asn Pro Asn Ala Asn Pro
1               5                   10                  15
Asn Ala Asn Pro Asn Ala Asn Pro Asn Ala Asn Pro Asn Ala Asn Pro
            20                  25                  30
Asn Ala Asn Pro Asn Ala Asn Pro Asn Ala Asn Pro Asn Ala Asn Pro
            35                  40                  45
Asn Ala Asn Pro Asn Ala Asn Pro Asn Ala Asn Pro Asn Val Asp Pro
    50                  55                  60
Asn Val Asp Pro
65
```

(2) INFORMATION FOR SEQ ID NO:14:

(i) SEQUENCE CHARACTERISTICS:
      (A) LENGTH: 20 base pairs
      (B) TYPE: nucleic acid
      (C) STRANDEDNESS: single
      (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO:14:

GATCCCGGGT GACTGACTGA      20

(2) INFORMATION FOR SEQ ID NO:15:

(i) SEQUENCE CHARACTERISTICS:
      (A) LENGTH: 16 amino acids
      (B) TYPE: amino acid
      (C) STRANDEDNESS: single
      (D) TOPOLOGY: unknown (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:15:

```
Gly Asn Val Gln Ala Ala Lys Asp Gly Gly Asn Thr Ala Ala Gly Arg
1               5                   10                  15
```

IMMUNO-POTENTIATING SYSTEMS FOR PREPARATION OF IMMUNOGENIC MATERIALS

This application is a continuation-in-part of application No. 08/29,666, filed Mar. 11, 1993, now abandoned, which is a continuation-in-part of application No. 07/336,952, filed Apr. 12, 1989, now abandoned, and a continuation-in-part of application No. 07/642,093, filed Jan. 16, 1991, now abandoned, which is a continuation application of application No. 07/065,440, filed Jun. 23, 1987, now abandoned.

FIELD OF THE INVENTION

This invention relates to means for improving immunogenic properties of peptides, polypeptides, and proteins by coupling with a hydrophobic anchor which may, in turn, be attached to proteosomes.

SUMMARY OF THE INVENTION

The instant invention provides an immunopotentiating system for enhancing immunogenic properties of peptides, polypeptides and protein. In some instances, amino acid sequences which have not been considered immunogenic or only weakly immunogenic may be rendered effectively immunogenic thereby. The synthesis of amino acid sequences is frequently economically advantageous over use of the natural antigen. Furthermore, proteins and peptides produced by genetic engineering which do not possess sufficient antigenicity may effect greater immune reaction when complexed with a hydrophobic anchor or "foot" attached to the amino acid sequences through one or more cystsines followed by dimerization or cyclization to form an enhanced peptide or protein structure which can be complexed with proteosomes. The resulting construct provides an immunogenic peptide comprising (a) peptides, protein fragment, and proteins having bonded thereto (b) a hydrophobic foot attached through cysteine(s) to the sequence to be render immunogenic, and wherein the hydrophobic foot is complexed to (c) a proteosome. "Proteins", in those instances when further definition is provided, should be interpreted to include polypeptides and protein fragments as well as entire proteins.

In a preferred embodiment, a method for production of immunogenic peptides comprises the steps of:

(a) replicating a core peptide or protein;
(b) reacting cysteine with the replicated peptide/protein to add at least one cysteine residue to said replicated peptide;
(c) reacting the replicated peptide/protein-cysteine with an aliphatic carboxylic acid or a hydrophobic peptide to add a hydrophobic foot to said replicated peptide/protein-cysteine to form an enhanced peptide structure;
(d) forming disulfide bonds in the enhanced peptide/protein structure to effect dimerization or cyclization of said enhanced peptide structure; and
(e) complexing the enhanced peptide/protein structure with a proteosome.

The constructs of the invention may be used for vaccines to protect against or treat disease conditions such as infectious diseases, malignancies, and toxic effects of chemicals and biologicals. Vaccines may also be used to prevent pregnancy.

Proteosomes are hydrophobic membranous, multimolecular membrane proteins. They may be obtained from any of a number of different organisms. Coupling may be accomplished by dialysis or lyophilization.

BACKGROUND OF THE INVENTION

The development of peptide subunits or recombinant protein vaccines to protect against pathogenic microorganisms and, of late, malignancies has been impeded by lack of sufficient immunogenicity in the peptides and proteins produced. Often the untoward effects resulting from exposure to an immunogen must be weighed against the adequacy of immunogenic properties. The presentation of small peptides, polypeptides and protein fragments to enhance immunogenicity without increasing undesired side effects from exposure to peptides, and protein fragments is an important area of investigation. There exists a paucity of carriers and adjuvants that are non-toxic and non-pyrogenic for human use. Furthermore, carriers that are safe for human use frequently cannot be efficiently complexed to the peptides to render them immunogenic without altering the proteins.

The development of substitutes for the whole organism or large proteins therefrom as vaccines is an important advance in biotechnology. Advances in biotechnology have made it increasingly possible to produce vaccines composed of amino acid sequences identical to conserved protein regions common to many strains of pathogens that may elicit cross-reacting antibodies. If the antigenicity can be improved by coupling with fragments that increase immunogenicity, improved vaccines can be developed.

Prior art of interest includes work of several researchers. Zollinger, et al., (*J. clin. Invest.*, 63, pp 836–848 (1979) and Frasch, et al. (in *The Pathogenic Neisseriae* pp 633–640, edited by G. Schoolnik, Praeger, New York (1985)) have used hydrophobic complexing to make outer membrane protein-polysaccharide vaccines. However, these researchers did not disclose the hydrophobic complexes disclosed herein.

Coon, et al (*Journal of Immunology*, Vol. 110, pp 183–190 (1973)) found that when lauric acid was heavily conjugated covalently to a large protein, bovine serum albumin, humoral immunogenicity was absent, but cell mediated immunity could be induced. In this work, lauric acid was not used to enhance humoral immunogenicity and peptides or protein fragments or hydrophobic complexes were not used.

Hopp disclosed (*Molec. Immunol.*, Vol. 21, pp 13–16 (1984)) addition of dipalmityl-lysine to a peptide to enhance its immunogenicity. The immunopotentiation reported by Hopp was exceedingly short-lived and induced peak titers that were only 5.1 fold greater than his control values. Furthermore, immunization as disclosed therein was carried out using Freund's adjuvant, which is not acceptable for use in humans.

Bessler, et al. (*Immunobiology*, Vol 170, p 239(1985)) reported using a tripalmitoyl pentapeptide analog of *E. Coli* lipoprotein as an adjuvant for sheep red blood cells, which were co-administered in a mixture. These researchers also covalently linked the tripalmitoyl pentapeptide to another peptide in order to boost the immune response. However, no enhancement of immunogenicity is evidenced therein.

Ballou (*Science*, Vol 228, pp 996–999(1985)) worked with naturally occurring antigens containing repeating epitopes such as those found in malaria to genetically engineer a cloned portion of the organism having 32 repeats of 4 amino acids (16 repeats of an 8 amino acid epitope with an additional 32 amino acid tetracycline-resistant marker peptide). This system was found effective in small animals when used with alum or Freund's adjuvant. These investigators did not, however, enhance immunogenicity in accord with the teachings of this invention.

Audibert, et al., (*Proceedings National Academy of Science, USA*, Vol. 79, pp 5042–5046 (1982)) used glutaraldehyde to polymerize a peptide, but found that the peptide was not immunogenic unless both a protein carrier such as bovine serum albumen or poly (LD-Ala)—ply (L-Lys) plus an adjuvant such as Freund's or muramyl dipeptide was used.

Liposomes have been considered as adjuvants. However, liposomes are entirely lipid and differ fundamentally from the system disclosed herein.

Morein and Simons (*Vaccine*, Vol. 3, pp 83–93 (1985)) described immunogenic complexes called iscoms between antigenic proteins and glycosides. The instant invention is fundamentally different from the constructs of Morein and Simons, since the present invention does not require glycosides.

The production of immune response to *P. falciparum*, the causative agent of malaria, is of particular concern. Worldwide, malaria is the most common serious infectious disease affecting humans. The *P. falciparum* has a tandemly repeated circumsporozoite (CS) tetrapeptide (NANP), which has been the subject of much vaccine research. G. N. Godson, in *Molecular Approaches to Malaria Vaccines*, discusses the repeated antigenic sequences in the circumsporozoite protein. When an animal is injected with sporozoites most of the antibodies it raises are directed against the CS protein, and specifically against the repeating epitope thereof.

European patent application EPA 191,748 (which is incorporated herein by reference) published Aug. 20, 1986 refers to an *E. coli* expression vector having a coding sequence for all or a portion of the repeat unit of the protein CS and discloses a process for purifying the immunogenic polypeptide from the *E. coli* culture.

European patent publication EPA 192,626, published Aug. 27, 1986 refers to an immunogenic polypeptide capable of conferring immunity to infection with *P. Faciparum* in mammals. The immunogenic polypeptide comprises four or more tandem repeat units of the CS protein. The repeat unit is a tetrapeptide having the sequence Asn Ala Asn Pro. Both of the EPA application identified above are incorporated herein by reference.

PCT published application WO87/06939 published Nov. 19, 187 teaches a process for isolating and purifying the CS protein expressed in recombinant *E. Coli*.

Dame, et al. discloses, in U.S. Pat. No. 4,707,357, an anti-malarial immunogenic stimulant comprising an immunogenic carrier and a peptide sequence of between two and 100 consecutive repeats of a sequence Asn X Y Pro, wherein X is Ala or Val and Y is Asn or Asp. The carriers disclosed therein include soluble molecules such as proteins and polysaccharides and particles such as liposomes and bacterial cells or membranes thereof. The peptide is attached to the carrier by an amide bond formed between a carboxylic acid or amino group of a carrier and an amino or carboxylic acid group of the peptide. The bonding may be through either an ether or ester linkage. Groups such as terminal diamines with one to 10 methylene carbons joining the amines are also recited as carriers. Preferred carriers disclosed are tetanus toxoid and amphoteric proteins having a lipophilic portion and a hydrophilic portion.

Patent publication WO86/05790, published Oct. 9, 1986, discloses immunogenic antigen-carrier protein conjugates for use as vaccines against malaria. The conjugates contain the peptide H-(Asn Ala Asn Pro)$_3$-OH, also designated (NANP)$_3$. This application also describes a preferred carrier such as tetanus toxoid. Other carriers include diphtheria toxoid and synthetic peptides and polymers comprising lysine and arginine groups. The peptide is coupled to the carrier using glutaraldehyde as a coupling reagent or adding a cysteine residue to the N-terminal of the peptide and using another conventional ester as a coupling reagent.

Achlessinger, et al., U.S. Pat. No. 4,769,235 (which is incorporated herein by reference) refers to eptiopes having the sequence of an immunodominant epitope from the repeat region of the CS protein which is shorter in length than the repeating unit of the CS protein. This peptide was active as a vaccine when coupled with a conventional carrier.

Patent publication WO86/00911 published Feb. 13, 1986 refers to the sue of a peptide an amino acid sequence Pro Asn Ala Asn repeated 23 or more times and adsorbed or coupled to a conventional vaccine carrier protein.

Alum absorbed vaccines containing various forms of the CS epitope have not been sufficiently immunogenic for general human use. Many protein carriers and liposomes recited in the prior art documents require lipid A or other adjuvants not acceptable for human use.

DETAILED DESCRIPTION OF THE INVENTION

The instant invention provides an immunopotentiating system which will render peptides (including small peptides) immunogenic and which will enhance the immunostimulating properties of larger peptides, proteins, and protein fragments. Immuno-stimulating can be defined as the capacity to induce a cytotoxic T cell lymphocyte response and/or an antibody response in a mammal. The desired amino acid sequences may be made by synthesis of amino acid sequences and/or polymerization, by extraction from the pathogens, or by recombinant means. Peptides or proteins may be characterized by variations from the immunostimulating sequences of the natural pathogens by addition, deletion, or insertion of other amino acids or by the attachment of additional sequences. The peptides may be positively or negatively charged or may be neutral. The peptides may be replicated to form tandem repeats.

The peptides and proteins used in the method of the invention may naturally contain cysteine residues. However, the natural presence of cysteine(s) is not required.

The hydrophobic foot which is attached to the immunostimulating sequence may vary in structure. A preferred hydrophobic foot comprises an aliphatic carbonyl group containing from 8 to 18 carbon atoms. In a preferred embodiment the group contains an alkanoyl moiety. A particularly preferred foot is lauroyl. Molecules of this type are easily added to the amino terminus of a synthetic peptide while the peptide is still on the resin used for synthesis. Peptides may be synthesized by the solid phase method described by Merrifield (*Soc.*, Vol 85, pp 21–49 (1963)). When a synthetic peptide is used, the alkanoyl, preferably as the chloride, can be reacted with the peptide on the resin.

The alkanoyl may also be added to the amino terminus by reaction of an alkanoyl acid such as lauric acid. To avoid side reactions, free amino groups may be blocked to assure that the alkanoyl group is attached to the end of the peptide. It is also possible to attach the alkanoyl group on the carboxy terminal using lysine as the carboxyterminal amino acid and reacting the alkanoyl with the epsilon amino group of the amino acid by conventional means.

The hydrophobic anchor may also be a hydrophobic peptide of about 3 to 50 amino acids (though preferably ≦24 amino acids) in length. In the instance where the immunogen is a peptide synthesized by sequential solid or liquid phase synthesis, the peptide may be added to the terminus (either amino or carboxy). A preferred hydrophobic peptide is a pentapeptide. The peptide Phe-Leu-Leu-Ala-Val (Seq. No. 1) is a preferred embodiment. The amino acids Tyr, Phe, Trp, Pro, Val, Ile and Leu are particularly useful in providing hydrophobicity. Hydrophobic amino acids of longer chain length can also serve the function of the hydrophobic foot so long as the length of the hydrophobic foot does not exceed about 24 amino acids. The peptide should not be rendered totally water insoluble in the presence of detergent.

When the peptides are synthesized, cysteine(s) may be added during the synthesis of the peptide. Cysteine may also be added to previously synthesized sequences by a carbodiimid reaction. The cysteine is useful for effecting dimerization or cyclization of the peptides. Unless reducing agents are present, dimerization occurs spontaneously following deblocking and cleavage of the peptide when one cysteine is present in the peptide. In a preferred embodiment one cysteine is located between the hydrophobic foot and the peptide epitope. When the construct contains two cysteines, cyclization is accomplished spontaneously in dilute solution after de-blocking and cleavage of the peptide. Ferricyanide oxidation of the peptide in the dilute solution causes formation intrachain (but not interchain) disulfide bonds.

In an embodiment of the invention, one cystsine residue is added to provide for dimerization of both the hydrophobic foot and the hydrophilic epitope. Dimerization appears to provide more stable binding to the proteosome by providing two hydrophobic feet for the epitope. The dimerized constructs also provide for more stable interaction with the antigen. The cysteine may be placed at either the carboxy or amino terminus of the epitope.

When the immunostimulating epitope is produced by genetic engineering means, the nucleotide sequence required for production of a peptide which is the hydrophobic foot and any desired cysteine(s) may be attached to the nucleotide giving rise to the immunostimulating epitope.

Materials and Methods Proteosome Preparation

Proteosomes were prepared from Group B type 2b meningococci. Proteosome preparation consisted of two stages. The first stage was done by either of two methods: (1) isolation of meningococcal outer membrane vesicles by extraction from an aqueous suspension of whole meningococci as previously described (Zollinger et al., *J. Clin. Invest.*, 63, page 836–848, 1979) or (2) collection of a direct bacterial cell extract precipitate. The direct cell extracts were obtained by extraction of packed bacterial cells for one hour at room temperature with one liter per 100 grams of cells of a solution containing 0.1M sodium acetate pH 5.0, 0.5M $CaCl_2$ and 3% Empigen BB. Ethanol was added to the mixture to a concentration of 20% v/v and the precipitate removed by centrifugation at 16,000 × g for 10 minutes. Additional ethanol was added to the supernatant to a final concentration of 45% and the precipitate, constituting the direct cell extract, was collected by centrifugation.

The second stage of the proteosome preparation consisted of isolating the outer membrane proteins from the other membrane components by dissolving either of the products from the first stage (i.e. either the vesicles or the direct cell extract) at a concentration of approximately 2 mg protein/ml in a buffer (hereafter referred to as TEEN-1%) containing 0.05 molar trishydrochloride (hydroxyacetyl amino methane), 0.15M NaCl, 0.01M EDTA (ethylene diamine tetra-acetate) and 1% Empigen BB (Albricht and Wilson, Cumbria, England) brought to pH 8.0. The proteins were then precipitated three times by addition of solid ammonium sulfate at 500 g/l of protein solution. The precipitates were collected by centrifugation at 30,000 × g for 20 minutes and redissolved at about 2 mg protein/ml in TEEN-1%. The final precipitate was dissolved with the aid of a water bath sonicator at about 2 mg/ml, centrifuged at 16,000 × g for 20 minutes to remove insoluble material and then dialyzed against TEEN-0.1% to remove any residual ammonium sulfate. (The final concentration of Emigen BB can be 0.1% to 1.0%). Products are stored at −20° C. (or, for short periods at 4° C.).

The proteosomes prepared from bacteria other than those prepared from meningococci may also be prepared and used by the same methodology.

In certain instances, the hydrophobic foot attached through the cysteine may be sufficient to provide needed antigenicity without use of proteosomes.

Epitope Replication

The peptide may be synthesized as a repeating unit wherein the sequences are in tandem as many times as synthesis will allow. Replicates of two to six times have been used with increasingly enhancing effects. Epitope replication enhances the immunogenicity of the peptide epitope. When the repeating units are complexed with a hydrophobic foot prepared with the methodology described below, a totally non-immunogenic peptide can be made immunogenic without added adjuvants and even without the proteosomes. Complexing the replicated peptides directly with proteosomes is also effective. When the cysteine is present with the replicated epitopes and the proteosomes, the system is optimal. Because complexing is dependent upon hydrophobic sites, the number of peptide molecules that can be complexed to the proteosome can be far greater than can be complexed by ordinary covalent bonding systems. When complexed with protein, 6–30 protein molecules may associate with each proteosome.

Any vaccine may be made by the method of the invention, including vaccines against parasitic, viral, bacterial, and fungal infection. Vaccines to prevent pathological response to toxic chemical and biological agents and against malignancies as well as vaccines to protect from pregnancy may be made by methods of the invention.

Preparation of Immunogenic Peptide Vaccines

Either of two complexing methods may be used, 1) Dialysis or 2) Lyophilization:

1. Dialysis a. Combine components in TEEN-1%: The proteosomes, stored in TEEN-1% buffer (see above) at a concentration $\geq 1$ mg/ml (usually 1.5–2.5 mg/ml), are added to a TEEN-1% solution of the peptide with the hydrophobic foot (and the cysteine &/or the replicated epitope as desired) in a beaker or test tube. Ratios of protein:peptide (weight:weight) that have been used have ranged from 1:1 to 1:40. The usual ratio has been 1:1 although, depending on the circumstances, 1:4 or higher may be preferable. Note that the concentration of the peptide in the solution prior to combination with proteosomes must be high enough so that the concentration of both the peptide and the protein in the combined mixture is $\geq 1$ mg/ml when the components are at equal ratios and, when the ratio is not 1:1, the concentration of the less concentrated component is $\geq 0.50$ mg/ml and preferably, $\geq 0.75$ mg/ml. For example, if the proteosomes are at 1.1 mg/ml, the peptide must be at 10 mg/ml prior to combining at a 1:1 ratio. While these minimal concentrations are not absolute and although successful vaccines have been made using protein concentrations that are more dilute (when the peptide:protein ratio is significantly >1:1) the method suggested here is more consistently successful.

b. Dialyze: The mixture was transferred to dialysis bags that, due to their low molecular weight cutoff, retain both the peptide and the protein while allowing the detergent (usually Empigen-BB) in the TEEN-1% to dialyze away. For this reason, Spectra-Por 6 (or 7) dialysis tubing with molecular weight cutoff of 1000 are routinely used to be certain that as much peptide as possible is retained for complexing to the proteosomes. The dialysis tubing (closed using special spectra-por closures) was washed just prior to use with pyrogen-free distilled water and then Phosphate Buffered Saline pH 8.5 (PBS-8.5). This latter buffer is the buffer against which the proteosome-peptide mixture was exhaustively dialyzed (e.g. at a ratio of 200–250:1 for 10 days changing the dialysis fluid daily) and consists of 0.025M $Na_2HPO_4$ plus 0.15M NaCl (normal saline). On the last day of dialysis, the buffer is changed to standard Phosphate buffered saline, PBS ($Na_2HPO_4 + NaH_2PO_4 + NaCl$ at pH 7.4). Under certain circumstances, dialysis may be able to be shortened e.g. to 5 days with 2 changes of fluid per day.

c. Collect vaccine: Solution was collected from dialysis bag(s). Dialysis bags were washed with 20% of their volume with PBS and the rise was combined with vaccine. The vaccine was filtered through a 0.22 µm filter (the vaccine may need to be pre-filtered through a 0.8 or 0.45 µm filter) or just a 0.45 µm filter. The protein content was measured (e.g. by optical density at 280 nm or Lowry assay), and samples were taken for amino acid analysis, HPLC and other analyses. The samples were then diluted with PBS to result in a 0.4 mg protein per ml solution. The final vaccine was then diluted 1:1 with either Normal Saline (with 0.02% merthiolate) to result in a 0.2 mg/ml solution which is administered at 0.5 ml per intramuscular dose. Alternatively, if desired, the vaccine can be adsorbed to alum by diluting 1:1 with a solution of alum instead of Normal Saline, allowing to sit at room temperature for 2 hrs. with occasional stirring and then at 4° C. for 3–18 hrs. It should be emphasized that the data indicate that the vaccine works perfectly well without alum and that the only reason for adding alum is to evaluate its role in the long term human response.

2. Lyophilization

Instead of combining the proteosomes and peptide (with a hydrophobic foot) in TEEN-1%, these components may be immunogenic when complexed by simply lyophilizing them together according to the following procedure:

Proteosomes are removed from TEEN-1% by precipitating them by adding three volumes of 100% ethanol to one volume of the proteosomes, allowing to stand at 4° C. for one hour and then centrifuging them at 800–1000 g for 15 minutes; washing the proteosomes three times by adding the same amount of 100% ethanol as previously used and re-centrifuging as before, then resuspending the proteosomes in PBS to a concentration of 2 mg/ml.

The peptide (with its hydrophobic foot and, if desired, cysteine and replicated epitopes) is then redissolved in PBS at 2 mg/ml (or another concentration as described above if a peptide:protein ratio >1:1 is desired). The dissolved peptide is added to to the proteosome suspension and mixed. The mixture is lyophilized and, following lyophilization, resuspended to 1 mg protein/ml using distilled water. The product is then filtered, analyzed, diluted and added to saline or alum as described above.

Addition of Cysteine

Adding the amino acid cysteine is employed in this system in either of two ways:

a. Dimerization: Adding one cysteine provides for dimerization of both the hydrophobic foot and the hydrophilic epitope. This component has been shown to be effective in enhancing the immunogenicity of a peptide in either of 3 ways: i) in conjunction with component the hydrophobic foot plus the proteosomes, ii) in conjunction with epitope replication, or iii) in conjunction with a hydrophobic foot and an epitope replication.

Dimerization provides two hydrophobic feet for the epitope, to provide more stable binding to the proteosomes or effect formation of auto-micelles. Furthermore, the two epitopes provided for by the dimerization can yield a more stable interaction with antigen recognition cells and may improve conformation of the peptide epitope.

b. Cyclization: Two cysteines are added to either end of the hydrophilic peptide epitope (i.e one cysteine between the epitope and the hydrophobic foot and one cysteine at the other end of the hydrophilic epitope). After the hydrophobic foot has been added the peptide may be deblocked and the peptide cyclized using an oxidizing agent such as ferricyanide.

Epitope Replication

Epitopes may be repeated in tandem as many times as synthesis will allow. Replication enhances the immunogenicity of the peptide epitope. When prepared with the methodology described below, a totally non-immunogenic peptide can be made immunogenic without added adjuvants and even without the proteosomes. Complexing the replicated peptides with proteosomes is also effective. Epitope replication may be used in conjunction with addition of cysteine for addition to a hydrophobic foot and/or proteosome.

The components of the inventive constructs can by complexed by any means known in the art. Any synthetic or cloned peptide can have a hydrophobic foot and cysteine added and therefore any peptide can be made immunogenic by this system which differs from chemical covalent complexing which depends on the correct chemistry to attach and orient the peptide epitope appropriately.

Proteosomes, in their native hydrophobic state, have special lymphocyte activating properties which allow them to act as both a protein carrier and an adjuvant. Since they are not chemically modified, but retain their multimolecularhydrophobic and membranous structure in the vaccine, their ability to immunopotentiate the immunogenicity of the peptides complexed to them is due to these special properties which are retained by the methods outlined above.

When using the hydrophobic foot with the cysteine and the replicate epitopes, peptide immunogenicity can be obtained even without addition of proteosomes. Toxicity and side effects would minimal.

EXAMPLES

The amino acid sequences of some of the peptides used to produce and operate this invention are given in TABLE 1. PepG is an example of a cyclic peptide—it has two cysteines which have been joined in a disulfide bond to make a cyclic loop in the peptide. PepM1 is non-cyclic, is without an added cysteine and contains the native epitope only once. PepCM1 has an added cysteine at the amino terminus as does pepCM3 and pepCM5. PepCM3 has three replicates of the native M epitope and pepM5 and pepCM5 have five such replicates. PepL1 has an epitope of only seven amino acids as does its cysteine-containing counterpart, CL1.

The data of tests done to produce and operate the invention are detailed in TABLES 2–4. All vaccines were prepared as described below. Briefly, the peptides, with or without added cysteines, were synthesized by standard solid phase technology. While still on the resin, a lauroyl group was added to the amino terminus as described below or the pentapeptide hydrophobic foot, Phe Leu Leu Ala Val (FLLAV) (Seq. No. 2), was added by simply continuing the synthesis. Except when noted otherwise, all vaccines were prepared by dissolving the peptides and/or the proteosomes in TEEN-1% detergent buffer and then exhaustively dialyzing away the detergent.

As shown in TABLE 2, both normal mice (BALB/c) and mice that are non-responsive to the adjuvant effects of lipopolysaccharide (C3H/HeJ), when immunized with either pepG alone, pepG in Freund's adjuvant, pepG with proteosomes (but without any hydrophobic foot), or either lauroyl-pepG or FLLAV-pepG without proteosomes were totally non-immunogenic (group 1, controls a–e). In marked contrast, pepG was made highly immunogenic by complexing it to proteosomes via either a lauroyl hydrophobic foot (groups 2 and 4) or via the pentapeptide hydrophobic foot (groups 3 and 5). This was demonstrated in both BALB/c mice (groups 2 and 3) and C3H/HeJ mice (groups 4 and 5).

Similarly, pepCL1 which is non-cyclic, was made immunogenic in both normal mice (group 15) and LPS non-responder mice (group 16). As expected, pepCL1 control groups were non-immunogenic (group 13, controls a–d).

The M1 epitope was tested for immunogenicity in the system both with an added cysteine (groups 9–12) and without the cysteine (groups 6–8). The cysteine was shown to be exceedingly important. High immunogenicity resulted from immunizing with either the standard 40 µg dose (group 11) or a sub-standard (8 µg) dose (group 12) of pepCM1 complexed to proteosomes. This peptide, lauroyl-pepCM1, was mildly immunogenic (after three immunizations) without proteosomes (group 10). In contrast, pepM1, lacking the cysteine, exhibited only the most minimal immunogenicity even with proteosomes (groups 7 and 8). The cysteine was considered to be important because its free sulfhydryl group causes dimerization of both the epitope and the hydrophobic foot. Dimerization of the epitope may allow better recognition by antigen processing cells whereas dimerization of the hydrophobic foot promotes better complexing to proteosomes.

The role of replicated epitopes in promoting immunogenicity in the system is detailed in TABLE 3. Once again, the peptides alone, even when lengthened by replicating the epitope three times, were non-immunogenic (group 17, control groups a–c). Nevertheless, immunization of normal BALB/c mice with the fatty acyl hydrophobic foot variant of this peptide, Lauroyl-pepCM3, resulted in high immunogenicity even without proteosomes when the vaccine was prepared by the standard dialysis method (group 18). Note that Lauroyl-pepCM3 was non-immunogenic when not dialyzed (group 19). It was found that dissolving the lipopeptide in detergent and then dialyzing away the detergent is effective for promoting formation of auto-micelles during the dialysis.

When Lauroyl-pepCM3 was complexed to proteosomes, immunogenicity was even further enhanced (group 20). This vaccine was also effective in C3H/HeJ mice again demonstrating that the ability of the proteosomes to enhance immunogenicity was not due to the <1% contaminating LPS in the proteosome preparation (group 24). It is believed that the lack of effect from the Lauroyl-pepCM3 in C3H/HeJ mice (group 23) was due to genetic restriction of recognition of the M1 epitope in these mice (and not insensitivity to the adjuvanticity of LPS) since a) Lauroyl-pepCM3 does not contain LPS and b) complexing the peptide to proteosomes which were able to provide carrier-like T-cell influence resulted in an immunogenic vaccine (group 24).

The optimal nature of the system when each of the four components (the proteosomes, hydrophobic foot, the cysteine and the replicated epitopes) were present was also demonstrated using pepCM3 with the FLLAV pentapeptide hydrophobic foot. Thus, FLLAV-pepCM3 was not immunogenic alone (group 21) whereas FLLAV-pepCM3 complexed to proteosomes was among the most immunogenic of all vaccines using the M1 epitope (group 22).

The role of the cysteine was also confirmed in conjunction with the replicated epitope and the lauroyl hydrophobic foot. The pepM5 control groups were non-immunogenic (group 25) as were the pepCM5 control groups (group 28). But when pepM5 was supplemented with the lauroyl hydrophobic foot (group 26) or both the lauroyl foot and proteosomes (group 27) only mild immunogenicity ensued even though the peptide was 47 amino acids long and had the M epitope repeated five times. In marked contrast, the Lauroyl-pepCM5 (which contains the added cysteine) was highly immunogenic (group 29) and complexing Lauroyl-pepCM5 to proteosomes further enhanced the immunogenicity (group 31) to maximal levels. When pepCM3 was incubated without dialysis, immunogenicity was markedly reduced (group 30). In C3H/HeJ mice, Lauroyl-pepCM5 was only minimally immunogenic (group 32) but Proteosome-Lauroyl-pepCM5 was clearly immunogenic (group 33). This data is consistent with the previous data obtained in C3H/HeJ mice as described above.

As shown in TABLE 4, effective proteosome-hydrophobic foot vaccines can also be made without using the dialysis method (described in the Methods section). Although the dialysis method appears to be optimal (groups 36–40), excellent immunogenicity can also be obtained by lyophilization of a saline or water mixture of the peptide (containing a hydrophobic foot, e.g. Lauroyl-CM1) with proteosomes that have previously been removed from the empigen detergent (group 35). Simply mixing the components together in saline, is not as effective as either lyophilization or dialysis although significant immunogenicity is attained this way (group 34). There may be applications in which the alternate methodologies described would be advantageous.

Also shown in TABLE 4 is the effect of varying the ratio of proteosome to peptide in the vaccine from 1:1 to 1:16 (groups 36–40). As is clearly evident, each of the vaccines was highly immunogenic. The implications of being able to use a ratio with more peptide per unit of protein are a) less protein needs to be administered in order to generate an effective immune response so that the possibility of side effects from the protein can be diminished and b) if a maximum amount of protein is administered, the amount of peptide that can be given is correspondingly increased. This increase in the amount of peptide that can be given may be critical to the development of a successful vaccine when the peptide epitope is particularly refractory to potentiation of immunogenicity.

TABLE 1

AMINO ACID SEQUENCES OF SEVERL TRYPANOSOMAL PEPTIDES TESTED IN PROTEOSOME-HYDROPHOBIC FOOT VACCINE SYSTEM

| No. | CODE | SEQUENCE |
|---|---|---|
| 1 | prpG | YGG(GCTQITEPTCN) (Seq. No. 3) <br> $\lfloor$__S=S__$\rfloor$ |
| 2 | pepM1 | YG(VPVAQTQTG) (Seq. No. 4) |
| 3 | pepCM1 | CYG(VPVAQTQTG) (Seq. No. 5) |
| 4 | pepCM3 | CYG(VPVAQTQTG)$_3$ (Seq. No. 6) |
| 5 | pepM5 | YG(VPVAQTQTG)$_5$ (Seq. No. 7) |
| 6 | pepCM5 | CYG(VPVAQTQTG)$_5$ (Seq. No. 8) |
| 7 | pepL1 | (KYNATKA) (Seq. No. 9) |
| 8 | pepCL1 | C(KYNATKA) (Seq. No. 10) |

The sequences within the parentheses are homologous with the sequences of the peptides in the native organism.

pepG = Tyr Gly Gly (Gly Cys Thr Gln Ile Thr Glu Pro Thr Cys Asn)
　　　　　　　　　　S=S
pepM1 = Tyr Gly (Val Pro Val Ala Gln Thr Gln Thr Gly)
pepCM1 = Cys Tyr Gly (Val Pro Val Ala Gln Thr Gln Thr Gly)
pepCM3 = Cys Tyr Gly (Val Pro Val Ala Gln Thr Gln Thr Gly)$_3$
pepM5 = Tyr Gly (Val Pro Val Ala Gln Thr Gln Thr Gly)$_5$
pepL1 = Lys Tyr Asn Ala Thr Lys Ala
pepCl1 = Cys Lys Tyr Asn Ala Thr Lys Ala

TABLE 2

ANTI-PEPTIDE ANTIBODY TITERS IN SERA OF MICE AFTER PRIMARY (1°), SECONDARY (2°) AND TERTIARY (3°) IMMUNIZATION WITH PEPTIDES WITH LAUROYL OR FLLAV HYDROPHOBIC FEET &/OR CYSTEINE &/OR PROTEOSOMES

| GRP NO. | MOUSE STRAIN | VACCINE | ANTI-PEPTIDE SERUM ANTIBODY TITERS POST IMMUNIZATION | | |
|---|---|---|---|---|---|
| | | | 1° | 2° | 3° |
| 1 | B, J | pepG Controls (a–e)* | <50 | <50 | <50 |
| 2 | B | Proteosome-Lauroyl-pepG | 400 | 204,800 | 204,800 |
| 3 | B | Proteosome-FLLAV-pepG | 400 | 12,800 | 102,400 |
| 4 | J | Proteosome-Lauroyl-pepG | 200 | 6,400 | 51,200 |
| 5 | J | Proteosome-FLLAV-pepG | 100 | 102,400 | 409,600 |
| 6 | B | pepM1 Controls (a–c)* | <50 | <50 | <50 |
| 7 | B | Lauroyl-pepM1 | <50 | 200 | 400 |
| 8 | B | Proteosome-Lauroyl-pepM1 | <50 | 400 | 400 |
| 9 | B | pepCM1 Controls (a–c)* | <50 | <50 | <50 |
| 10 | B | Lauroyl-pepCM1 | <50 | <50 | 3,200 |
| 11 | B | Proteosome-Lauroyl-pepCM1 | 400 | 102,400 | 409,600 |
| 12 | B | Proteosome-Lauroyl-pepCM1 (8 ug) | 200 | 102,400 | 204,800 |
| 13 | B, J | pepCL1 COntrols (a–d)* | <50 | <50 | <50 |
| 14 | B | Lauroyl-pepCL1 | 800 | 400 | 800 |
| 15 | B | Proteosome-Lauroyl-pepCL1 | 50 | 200 | 51,200 |
| 16 | J | Proteosome-Lauroyl-pepCL1 | 50 | 400 | 51,200 |

Groups of 5–8 BALB/c (B) or C3H/HeJ (J) mice were immunized ip on weeks 0, 3 & 7 with vaccines containing 40 ug of peptide; sera, obtained 2–3 weeks after each immunization, were tested in an ELISA for IgG antibodies against the homologous peptide (either pepG, pepM1 or pepL1). Titers are the highest serum dilutions which had ELISA values that were a) more than 0.1 o.d. units and b) twice the value of pre-vaccination sera diluted 1:50.

*Each of the Control groups consisted of 5 mice immunized with either a) peptide alone, b) peptide in Freund's adjuvant, c) peptide and Proteosomes without hydrophobic feet, d) Lauroyl-peptide without proteosomes, and e) FLLAV-peptide without Proteosomes.

TABLE 3

ANTI-PEPTIDE ANTIBODY TITERS IN SERA OF MICE AFTER PRIMARY (1°), SECONDARY (2°) AND TERTIARY (3°) IMMUNIZATIONS WITH PEPTIDES WITH LAUROYL OR FLLAV HYDROPHOBIC FEET AND/OR CYSTEINES AND/OR REPLICATED EPITOPES AND/OR PROTEOSOMES

| GRP NO. | MOUSE STRAIN | VACCINE | ANTI-PEPTIDE SERUM ANTIBODY TITERS POST IMMUNIZATION | | |
|---|---|---|---|---|---|
| | | | 1° | 2° | 3° |
| 17 | B, J | pepCM3 Control groups (a–c) | <50 | <50 | <50 |
| 18 | B | Lauroyl-pepCM3 | 400 | 102,400 | 102,400 |
| 19 | B | Lauroyl-pepCM3 (non-dialyzed) | <50 | <50 | 100 |
| 20 | B | Proteosome-Lauroyl-pepCM3 | 6,400 | 102,400 | 409,600 |
| 21 | B | FLLAV-pepCM3 | <50 | 50 | 50 |
| 22 | B | Proteosome-FLLAV-pepCM3 | <50 | 204,800 | 6,553,600 |
| 23 | J | Lauroyl-pepCM3 | <50 | 50 | 50 |
| 24 | J | Proteosome-Lauroyl-pepCM3 | <50 | 800 | 204,800 |
| 25 | B | pepM5 Control groups (a–c)* | <50 | <50 | <50 |
| 26 | B | Lauroyl-pepM5 | 200 | 400 | 12,800 |
| 27 | B | Proteosome-Lauroyl-pepM5 | 200 | 1600 | 12,800 |
| 28 | B, J | pepCM5 Control groups (a–c)* | <50 | <50 | <50 |
| 29 | B | Lauroyl-pepCM5 | 800 | 204,800 | 204,800 |
| 30 | B | Lauroyl-pepCM5 (non-idalyzed) | 100 | 12,800 | 25,600 |
| 31 | B | Proteosome-Lauroyl-pepCM5 | 400 | 25,600 | 3,276,800 |
| 32 | J | Lauroyl-pepCM5 | 50 | 100 | 100 |
| 33 | J | Proteosome-Lauroyl-pepCM5 | 200 | 25,600 | 51,200 |

Groups of 5–8 BALB/c (B) or C3H/HeJ (J) mice were immunized ip with vaccines containing 40 μg of peptide on weeks 0, 3, & 7; sera, obtained 2–3 weeks after each immunization, were tested i an ELISA for anti-pepM1 IgG. Titers whowm are the highest serum dilutions with ELISA values that were both a) >0.1 o.d. units and b) twice the value of pre-vaccination sera diluted 1:50.

*Each of the Control groups consisted of 5 mice immunized with either a) peptide alone, b) peptide in Freund's adjuvant, c) peptide and Proteosomes without hydrophobic feet, d) Lauroyl-peptide without proteosomes, and 3) FLLAV-peptide without Proteosomes.

*The detergent (empigen) was removed from the proteosomes by ethanol precipitation and the proteosomes were washed and resuspended in saline prior to mixing (group 34) or lyophilization (group 35) with a saline solution of pepCM1.

Groups of 5–8 C57B1/6 mice were immunized ip on weeks 0, 3 & 7 with 40 ug of peptide and the corresponding amount of proteosomes; sera, obtained 2–3 weeks after each immunization, were tested in an ELISA for IgG antibodies directed against the homologous peptide, pepM1; titers whowm are the highest serum dilutions that had ELISA values that wereboth a) greater than 0.1 o.d. units and b) twice the value of pre-vaccination sera diluted 1:50.

TABLE 4

EFFECTS OF THE COMPLEXING METHOD AND THE PROTEOSOME:
PEPTIDE RATIO ON THE ABILITY OF PROTEOSOMES TO ENHANCE THE
IMMUNOGENICITY OF PEPTIDE LAUROYL-CM1

| GRP No. | COMPLEXING METHOD* | PROTEOSOME:PEPTIDE RATIO | ANTI-PEPTIDE SERUM ANTIBODY TITERS POST IMMUNIZATION | | |
|---|---|---|---|---|---|
| | | | 1° | 2° | 3° |
| 34 | Mix | 1:1 | 400 | 6,400 | 51,200 |
| 35 | Lyophilize | 1:1 | 800 | 12,800 | 409,60) |
| 36 | Dialyze | 1:1 | 12,800 | 409,600 | 6,553,600 |
| 37 | Dialyze | 1:2 | 25,600 | 819,200 | 819,200 |
| 38 | Dialyze | 1:4 | 6,400 | 819,200 | 1,638,400 |
| 39 | Dialyze | 1:8 | 12,800 | 819,200 | 1,638,400 |
| 40 | Dialyze | 1:16 | 51,200 | 1,638,400 | 3,276,800 |

Groups of 5–8 BALB/c or C3H/HeJ mice were immunized ip on weeks 0, 3 & 7 with vaccines containing 40 ug of peptide; sera, obtained 2–3 weeks after each immunization, were tested in an ELISA for IgG antibodies against meningococcal outer membrane proteins. Titers shown are the highest serum dilutions obtained after two or three immunizations which had ELISA values that were a) more than 0.1 o.d. units & b) twice the value of pre-vaccination sera diluted 1:50.

TABLE 5

ANTI-MENINGOCOCCAL IgG ANTIBODIES IN SERA OF MICE
IMMUNIZED AND BOOSTED WITH PROTEOSOME-
HYDROPHOBIC FOOT-PEPTIDE VACCINES USING EITHER
THE LAUROYL OR THE FLLAV HYDROPHOBIC FOOT

| GRP NO | VACCINE | ANTI-MENINGOCOCCAL IgG ANTIBODY TITERS |
|---|---|---|
| 1 | Controls | <50 |
| 2 | Proteosome-Lauroyl-pepG | 102,400 |
| 3 | Proteosome-FLLAV-pepG | 409,600 |

Groups of 5–8 BALB/c or C3H/HeJ mice were immunized ip on weeks 0, 3 & 7 with vaccines containing 40 ug of peptide; sera, obtained 2–3 weeks after each immunization, were tested in an ELISA for IgG antibodies against meningococcal outer membrane proteins. Titers shown are the highest serum dilutions obtained after two or three immunizations which had ELISA values that were a) more than 0.1 o.d. units & b) twice the value of pre-vaccination sera diluted 1:50.

Longer peptides and proteins may also be potentiated by methods of the invention. Many extracted or cloned polypeptides (especially transmembrane polypeptides) naturally have hydrophobic ancors which are frequently 15 to 30 amino acids long. The immunogenicity of such polypeptides may also be enhanced by extending the native hydrophobic anchor or by adding another hydrophobic anchor according the methods of the invention. A preferred decapeptide, Gly-Gly-Tyr-Cys-Phe-Val-Ala-Leu-Leu-Phe (Seq. No. 11) is a preferred embodiment because of appropriate size and composition to allow for easy purification of a recombinant anchored protein. Native sequences can be of such length and composition as to hinder extraction and purification.

The hydrophobic anchor sequence is preferably added to the carboxy-terminus of the selected recombinant protein by genetic engineering methods. Hence, the polynucleotide that encodes the anchor can be added to the 3' end of the gene that encodes for the desired recombinant protein. Alternatively, the polynucleotide that encodes the anchor may also be added to the 5' end of the selected protein. As another embodiment, the polynucleotide that encodes the anchor may be added to both the 5' and 3' termini of the sequence that encodes the selected protein. For conventional techniques to accomplish construction of these vectors, see T. Maniatis, et all, *Molecular Cloning (A Laboratory Manual)*, Cold Spring Harbor Laboratory (1982). The constructs can be complexed to the proteosomes by dialysis or lyophilization as described above in methods for preparation with peptides. Similarly, the hydrophobic foot may be attached by the methods indicated for attachment to peptides as an alternative to production in a recombinant molecule as described above.

Ratios of proteosomes to anchored recombinant protein (weight:weight) ranges from 1:1 to 1:20. Preferred ratios are between 1: and 1:3 for polypeptides or proteins.

Since hydrophobic complexing is more physical than chemical, and since hydrophilic protein epitopes are always left conserved, exposed, and unaltered, antibodies generated against the epitope will easily recognize the protein or epitope therein and will, therefore, be functional against the pathogen from which the epitope is derived.

Vaccine compositions of the invention may be introduced into the patient by conventional means, including parenteral routes (for example, subcutaneous, intradermal, intramuscular) and by direct application to mucous membranes. Lyophilized compositions may be "snorted" into the nasal cavity. Dosage will depend on the particular agent administered.

An example of the value of the method of the invention is illustrated by use with a recombinant protein (R32RL), a 384 base pair fragment encoding 32 tetrapeptide repeats [(Asn Ala Asn Pro)is. (Asn Val Asp Pro)]$_2$ of the *P. falciparum* CS protein, rendered immunogenic by adding the hydrophobic foot, cysteine-containing decapeptide anchor to its carboxy terminus to create R32Ft. R32Ft is immunogenic in vaccine testing when used alone and such immunogenicity is markedly enhanced when it is complexed to proteosomes via the added hydrophobic decapeptide anchor described above. (It should be understood that the examples provided herein are illustrative only and do not limit the scope of the present invention to the specific vaccine components nor the particular recombinant protein used therein.

Construction of the Anchored Recombinant Protein, R32Ft

Ten micrograms of expression vector pAS1 (ATCC 39262, more fully described in U.S. Pat. No. 4, 578,355, which is incorporated herein by reference) was digested with restriciton endonuclease BamHI (25 units) in 200 μl medium buffer [comprising 50mM Tris, 5mM NaCl, 1 mM dithiothreitol (DTT), and 10 mM MgCl, having a pH of 7.5] for 1.5 hours at 37 °C. One hundred nanograms of the BamHI-cut pAS1 was ligated with 20 ng of a synthetic linker having the following sequence:

5'-GATCCCGGGTGACTGACTGA -3' (Seq. No. 14)
3'- GGCCCACTGACTGACTCTAG-5'

The resulting plasmid, pT17, was identified with one linker inserted into the BamHI site of pAS1. This vector retains the BamHI site, introduces a unique SmaIsite, and results in the insertion of TGA termination codons in all three reading frames downstream of the ATG initiation codon of the cII ribosome binding site.

Fourth micrograms of purified pUC8 clone 1, a pUC8 clone [Viera, et al., Gene, 19:259 (1982)] containing the CS protein coding sequence as a 2337 base pair EcoRI fragment of gamma-mPF1 inserted into the EcoRI site of pUC8 [Dame eta;., Science 225:593 (1984)] was digested with restriction endonuclease XhoII in 400 μl of medium buffer for 1.5 hours at 37° C. The resulting 192 base pair fragment, encoding 16 tetrapeptide repeats [(asn-Al-Asn-Pro)$_{15}$-(Asn-Val-Asp-Pro)]$_2$ (Seq. No. 13) of the *P. falciparum* CS protein, was isolated by electrophoresis on a 5% polyacrylamide gel (PAGE) and recovered by electroelution.

Expression vector pT17 (10 μg) was digested with restriction endonuclease BamHI (25 units) in 200 μl medium buffer (described above) for 1.5 hours at 37° C. The Xho II CS protein gene fragment (1 230 g) was then ligated into this vector (100 ng) in 30 μl ligase buffer (comprising 50 mM Tris, 1 mM DTT, 10 mM MgCl$_2$, and 100 μM rATP, having pH of 7.5) with one unit of T4-DNA ligase for 16 hours at 4° C.

The ligation mixture was transformed into *E. coli* strain MM294CI+[Smithkline French]. Ampicillin resisitant colonies were obtained and screened for insertion of the Xho II gene fragment into pT17. A plasmid with the correct construction, pR16, was identified and transformed into *E. coli* strain MM294CI+.

Expression vector pR16 was digested with restricition endonuclease BamHI as described above and a second Xho II CS protein gene fragment ligated into the vector. The ligation mixture was transformed into *E. coli* strain MM294CI+, ampicillin resistant colonies thereof selected and a plasmid with the correct construction, pR32, containing 32 repeats of the CS tetrapeptide, identified and transformed into *E. coli* strain MM294CI+.

Expression vector pR32 (10 μg) was digested by restriction endonuceases SmaI and SalI in 200 μl medium buffer (described above) for 1.5 hours at 37°

C. The synthetic DNA hydrophobic decapeptide anchor sequence (1 μg) identified below was then added and ligated to the SmaI/SalI cut pR32 (100 μg) in 30 μl ligase buffer with one unit of T4-DNA ligase at 4° C. for 16 hours. The hydrophobic decapeptide sequence was 5' GGT GGT TAC TGC TTC GTT GCT CTG CTG TTC TGA G (Seq. No. 12) 3' CCA CCAATG ACGAAG CAA CGA GAC GACAAG ACT CAGCT The ligation mixture was transformed into *E. coli* strain MM294CI+. Ampicillin resistant colonies were obtained and screened for the insertion of the decapeptide into pR32. A plasmid with the correct construction, pR32Ft, was identified and transformed into *E. coli* strain AR58 (CI$^{857}$) and tested for expression of the gene product.

Cells were grown in Luria-Bertani Broth (LB) at 32° C. to an absorbance of 650 nm ($A_{650}$) of 0.6 and temperature induced at 42° C. for 3 hours to turn on transcription of the PL promoter of the expression plasmid and subsequent translation of the CS protein derivative. Cells were sampled in 1 ml aliquots, pelleted, resuspended in lysis buffer (comprising 10 mM Tris-HCl, 25% (vol/vol) glycerol, 2% 2-mercaptoethanol, 2% sodium dodecyl sulfate (SDS), and 0.1% bromophenol blue, having a pH of 7.8) and incubated in a 105° C. heating block for 5 minutes. Proteins were separated by SDS-PAGE (12% acrylamide, 30:0.8 acrylamide:bisacrylamide ratio).

Protein produced from *E. coli* was detected by Western Blot analysis as described below in Example 2.

Purifiecation of R32Ft

The R32Ft peptide was purified from the expression system of the previous example as disclosed below. All operations were performed on ice unless stated otherwise.

Three 20-g *E coli* frozen pellets [SmithKline Laboratories] were combined and thawed by suspending inot 240 ml of 50 mM Tris [Bio-Rad], 2 mM ethylenediamine tetraacetic acid (EDTA) [Signma], 5% glycerol [Sigma] at pH 8.0 and stirring for one hour. Grade I lysozyme (48 mg, final concentration 0.2 mg/ml) and phenylmethyl sulfonyl floride (PMSF) [Signma], 1 ml at a concentration of 34 mg/ml in absolute ethanol were added and the suspension stirred for 30 minutes. The lysate was blended for 1 one-minute intervals in a blender and sonicated for 3 one-minute intervals (Artek, model 300, medium probe). Sodium deoxycholate (DOC) [Sigma] was added to a final concentration of 0.1% (w/v). The suspension was stirred for 30 minutes, then centrifuged for 1 hour at 12000 × g.

The supernatant was heated in a boiling water bath for 5 minutes with stirring, cooled for one hour at ambient temperature, and then centrifuged at 12000 × g. Crude antigen was precipitated in a 10% to 40% ammonium sulfate peellet. The pellet was resuspended in 25 ml phosphate buffered saline (PBS) and dialyzed extensively against PBS (Spectropor tubing, NW cutoff 3000).

The sample was acidified to pH 2.0 by dropwise addition of 10% trifluoroacetic acid (TFA), stirred for 1 hour and centrifuged for 30 minutes at 12000 × g. The supernatant was collected and dialyzed into 10% PBS and lyophilized to reduce the volume to 5 ml. The solution was recentrifuged to clarify.

Final purification was carried out by high performance liquid chromatograph (HPLC) using a Waters system, including tow model 510 pumps, and model 481 detector, automated gradient conntroller and an LKB model 2212 Helirac fraction collector with a semi-prep C-3 reverse phase column. Protein elution was monitored at 214 nM. Buffer A was 0.05% TFA/water and Buffer B was 0.05% TFA in 90% MeCN/water. Flow was 9.5 ml/min. The gradient started at 70% A, proceeded linearly to 50% A in 20 minutes and was washed with 70% B for 8 minutes.

Proteins were neutralized by collection into equal volumes of saturated ammonium bicarbonate and assayed using a quick ELISA system. Protein peaks with strong ELISA activity were lyophilized and characterized by Western blot and amino acid analysis. Two peaks with activity were eluted consistently at 45% and 48% B. The proteins were indistinguishable by amino acid analysis and Western blot. Both exhibited a single band migrating at 54 kd. Amino acid analsysis was identical.

The anchored recombinant proteins were complexed to the protesomes via dialysis. Proteosomes in a concentration of 0.5–2.5 mg/ml were added to solution of the recombinant protein with the hydrophobic foot to provide ratios of proteosomes to anchored recombinant protein (w/w) range of 1:1 to 1:20. The material was dialized in accord with the teachings above.

Animal Immunizations

Groups of mice were dosed with 50 µg proteosomes with 50–100 µg R32Ft or with 50–100 µg R32Ft without the proteosomes. Adll injections were administered using saline as the carrier. No additional adjuvants were used. Analysis of pooled sera from the groups of mice showed that while the recombinant R32Ft alone was effective, the recombinant R32Ft complexed with the proteosome was at least 16 fold as effective as a vaccine. Both C57B1 strain and BALB/c mice responded to the vaccines. When the animals were given booster shots (up to two boosters given) the improved immune response was seen in all instances.

Individual rabbits were dosed with 100–200 µg R32Ft (recombinant) alone or complexed to 100 µg/dose of proteosomes. The recombinant R32Ft with the proteosomes was about 10 fold as effective as the R32Ft having hydrophobic foot but no proteosome complexed thereto.

Proteosomes can also be complexed with the anchored recombinant protein by lyophilization in accord with the methods taught above.

Previous attempts to immunize mice with the protein R32LR (without the hydrophobic sequence) showed that protein to be non-immunogenic or, if given with complete freunds adjuvant or alum, to be only poorly immunogenic.

gp160 Vaccine Against AIDS

Proteosomes were constructed as indicated above and were stored at −70° C. in small aliquotes at concentration of >5 mg/ml (usually 6–7 mg/ml) in TEEN buffer containing 0.1% ( or, on occasion, 1%) Empigen BB detergent. The proteosomes were defrosted immediately before use.

Prior to using the pg160, which was obtained containing 0.01%TWEEN detergent the gp160 was prepared in accord by one of the two following methods:

1) Dialysis: Seven ml of pg 160 containing TWEEN was dialyzed across a SpectraPor membrane with molecular weight cut-off (MWCO) of 100,000 daltons against two liters of 0.1M Tris buffered normal saline, pH 8.0 at 4° C. for four days, changing the buffer solution once per day. As an example, in one instance, 10.7 mg of gpl60 in 0.1M Tris buffered saline was used of a stock of 0.54 mg/ml concentration in a volume of 19.8 mls. Next, Empigen BB (stock solution of 30% was added to result in a final concentration of 1% of Empigen (0.64 ml).

The proteosomes were added to provide a 1:1 ratio (weight:weight) so that 10.7 mg of 6.7 mg/ml stock in 1.6 ml was added to result in a final concentration of 0.485 mg/ml of gp160 and proteosomes. The resulting product was dialyzed across a 1000 MWCO spectraPor 6 or 7 membrane for 10 days at 4° C. against Tris buffered saline changing the buffer daily.

2) Centrifugal Dialysis: Centriprep 30 tubes were used to simultaneously remove the TWEEN and concentrate the gp160 stock from 0.7 mg/ml to >4 mg/ml by diluting 15 mls of the 0.7 ml stock with 5 mls of Tris buffered saline to result in a concentration of 0.5 mg/ml. This was centrifuged at 2,000 g in a Beckman centrifuge for 15 minutes at 4° C. to result in 10 ml of partially concentrated gp160. This was diluted to 20 mls and recentrifuged as above to result in 10 ml volume. The resulting concentrate was rediluted with Tris buffered saline to 30 mls and recentrifuged as above to result in a final volume of 3.2 mls with a gp160 concentration of 4.25 mg/ml (analyzed spectrophotometrically at 0.280) and with an estimated 99.999% TWEEN removal and 94% recovery of gp160. For example, 7.2 mg of gpl60 in 0.1M Tris buffered saline was used of a stock of 4.2 mg/ml concentration in a volume of 1.7 mls. Next, Empigen BB (stock solution of 30% was added to result in a final concentration of 1% of Empigen (0.08 ml).

The proteosomes were added to provide a 1:1 ratio (weight:weight) so that 7.2 mg of 6.7 mg/ml stock in 1.1 ml was added to result in a final concentration of 2.5 mg/ml of gp160 and proteosomes. The resulting product was dialyzed across a 1000MWCO spectraPor 6 or 7 membrane for 10 days at 4° C. against Tris buffered saline changing the buffer daily.

The pg160 is a much larger than the R32ft disclosed herein. The gp160 is a transmembrane protein. Furthermore, it naturally forms trimers that make its molecular weight even larger. The antigenic compositions containing gp160 complexed to proteosomes can be enhanced by addition of adjuvants such as alum. It has also been discovered that sub micron emulsions enhance immunogenicity. Table 6 gives a comparison of ELSA analysis of sera from rabits immunized 4 times i.m. with 85 µg of gp160 formulated with alum, proteosomes plus alum, or proteosomes plus sub-micron emulsions:

TABLE 6

ENHANCED SERUM ANTIBODY RESPONSE TO THRE GP160 ANTIGENS INDUCED IN RABBITS BY FORMULATING GP160 WITH PROTEOSOMES PLULS ALUM COMPARED TO GP160

| Vaccine | Geometric mean of serum IgG titers | | |
|---|---|---|---|
| | gp160 | gp41 | Alex 10* |
| gp160/alum | 30,274 | 680 | 1 |
| gp160/proteosome/alum | 51,112 | 565 | 693 |
| gp160/proteosome/SME | 104,664 | 1,538 | 200 |

*Alex 10 is a significant epitoope of gp120.
Data shows that gp160/proteosome/adjuvant provides vaccine with improved antigenic effects.

Leishmania Vaccine

Mice immunized and then infected with L. major in a murine model of cutaneous leishmaniasis having a lauryl or lauryl-cysteine conjugated to the amino terminus was assessed for cell mediated immune response. Vaccines will consist of lauryl or lauryl-cysteine conjugated to a selected synthetic gp63 peptide 467–482 having the structure Gly Asn Val Gln Ala Ala Lys Asp Gly Gly Asn Thr Ala Ala Gly Arg (Seq. No. 15) The peptide covalently conjugated to lauryl-cysteine protected against severe leishmania cutaneous lesions with an average of 81% reduction of lesions in 3 separate experiments. This occurred even when giving the lauryl-cysteinyl-peptide in saline without other adjuvants whereas the cysteinyl-peptide or the peptide without the added lauryl moiety was ineffective. Addition of proteosomes or other peptides did not further enhance protection. Proliferative studies were negative. Gene bank analysis of this peptide revealed a striking homology with a human integrin molecule responsible for localization of cellular elements in the inflammatory process indicating that the parasite may use immune mimicry to avoid host immune defense mechanisms. This peptide may therefore have wide application in ameliorating pathologic cellular immune responses caused by other forms of leishmania or other parasites or bacteria such as mycobacteria where CMI protection is important.

Proteosomes confer intranasal immunogenicity on formalinized toxoid of Staphylococcal Enterotoxin B (SEB) when formulated with proteosomes. In mice anti-SEB respiratory IgA and serum IgG were induced when the complexed compositions in saline were administered intranasally. The proteosome-toxoid vaccine also showed enhanced immunogenically when given parenterally. The proteosome-toxoid vaccine was made by the dialysis method as described. The toxoid and proteosomes were mixed in the presence of 1% buffered detergent (Empigen) and dialyzed. Mice immunized intranasally with proteosome-toxoid vaccines were significantly protected (p<0.0117) against systemic challenge with >4 LD100 of SEB using the D-galactosamine SEB challenge model. Mice immunized parenterally with proteosome-toxoid vaccines responded with high levels of anti-SEB serum IgG which were further enhanced by adjuvant in with alum. Using the D-galactosamine model, 98% of the 55 mice immunized parenterally with these vaccines that induced high anti-SEB serum IgG were protected against parenteral SEB challenge whereas mice immunized with the formalinized toxoid in saline or alum that had titers <55,000 were significantly less protected.

As indicated, the methods of the invention are appropriate for use both with addition of the hydrophobic foot. However, when there is a hydrophobic moiety in or associated with the peptide, it is not necessary to synthetically add the hydrophobic foot.

The examples provided herein are for exemplification only, and are not to be construed as suggesting limitation thereto.

I claim:

1. A construct comprising:
   (1) a protein, protein fragment, polypeptide or peptide,
   (2) a hydrophobic anchor, and
   (3) a proteosome.

2. A construct of claim 1 wherein the hydrophobic anchor is attached to the protein, polypeptide, or peptide through one or more cysteines.

3. A construct of claim 2 wherein a disulfide bond exists between two cysteine residues.

4. A construct of claim 1 wherein the hydrophobic anchor is an alkanoyl moiety.

5. A construct of claim 1 wherein the hydrophobic anchor is a lauroyl moiety.

6. A construct of claim 5 wherein the hydrophobic anchor is a peptide.

7. A construct of claim 1 containing the peptide Gly Asn Val Gln Ala Ala Lys Asp Gly Gly Asn Thr Ala Ala Gly Arg (Seq. No. 15).

8. A construct of claim 1 wherein the hydrophobic anchor is a lauryl moiety bound to the peptide through a Cysteine.

9. A method of making a construct of claim 1 comprising the steps of:
   (1) replicating a core peptide or protein;
   (2) reacting said replicated peptide or protein with an aliphatic carboxylic acid or a hydrophobic peptide to add a hydrophobic anchor to said peptide or protein; and
   (3) complexing the structure formed in step (2) with a proteosome.

10. A method of claim 9 wherein, after step (1) and before step (2), the peptide or protein is reacted with cysteine to add at least one cysteine residue to said replicated peptide or protein.

11. A method of step 9 wherein the product of step (2) is complexed with the proteosome by dialysis.

12. A method of claim 9 wherein the product of step (2) is complexed to the proteosome by lyophilization.

13. A construct of claim 1 containing the peptide Phe Leu Leu Ala Val (Seq. No. 1).

14. A construct of claim 1 containing the Leishmania gp63 peptide.

15. A construct comprising:
(1) a protein, polypeptide or peptide,
(2) a hydrophobic anchor, said anchor being a peptide of formula
Gly Gly Tyr Cys Phe Val Ala Leu Leu Phe (SEQ ID NO: 11), and
(3) a proteosome.

* * * * *